United States Patent [19]

Helfer et al.

[11] Patent Number: 4,810,653

[45] Date of Patent: Mar. 7, 1989

[54] CUVETTE WITH NON-FLEXING THERMALLY CONDUCTIVE WALL

[75] Inventors: Jeffrey L. Helfer; Johannes J. Porte, both of Webster; David H. Middleton, Rochester, all of N.Y.

[73] Assignee: Eastman Kodak Company, Rochester, N.Y.

[21] Appl. No.: 123,752

[22] Filed: Nov. 23, 1987

[51] Int. Cl.$^{4}$ ................................................ C12M 1/02

[52] U.S. Cl. .................................... 435/316; 435/287; 356/246

[58] Field of Search ............... 435/287, 292, 296, 316; 356/246; 215/1 R, 1 C; 220/86 R; 422/58, 61, 102

[56] References Cited

U.S. PATENT DOCUMENTS

| | | | |
|---|---|---|---|
| 3,691,017 | 9/1972 | Brown et al. . | |
| 4,088,448 | 5/1978 | Lilja et al. | 356/246 |
| 4,405,235 | 9/1983 | Rossiter | 356/246 |
| 4,426,451 | 1/1984 | Columbus | 435/287 |

*Primary Examiner*—Larry Jones

*Attorney, Agent, or Firm*—Dana M. Schmidt

[57] ABSTRACT

There is disclosed a cuvette constructed with an improved sample fluid thermal time constant, featuring a flexible heat transfer wall. To prevent such wall from deforming under pressure generated at high processing temperatures, thereby reducing heat transfer efficiency, the opposite wall is constructed to have a flexural strength that is sufficiently less than that of the heat transfer wall. This causes flexing to occur in the opposite wall, under pressure, rather than the heat transfer wall.

3 Claims, 1 Drawing Sheet

CUVETTE WITH NON-FLEXING THERMALLY CONDUCTIVE WALL

FIELD OF THE INVENTION

This invention relates to cuvettes in which reactions are undertaken in liquids confined within the cuvette, and particularly those reactions requiring carefully controlled temperatures and a rapid rate of heat transfer to or from the cuvette.

BACKGROUND OF THE INVENTION

Although this invention is not limited to cuvettes used for nucleic acid amplification, the background is described in the context of the latter, as such amplification led to the invention.

Nucleic acid amplification generally proceeds via a particular protocol. One useful protocol is that set forth in U.S. Pat. No. 4,683,195. Briefly, that protocol features, in the case of DNA amplification, the following:

(1) A complete DNA double helix is optionally chemically excised, using an appropriate restriction enzyme(s), to isolate the region of interest.

(2) A solution of the isolated nucleic acid portion (here, DNA) and nucleotides is heated to and maintained at 92°–95° C. for a length of time, e.g., no more than about 10 minutes, to denature the two nucleic acid strands; i.e., cause them to unwind and separate and form a template.

(3) The solution is then cooled through a 50°–60° C. zone to cause a primer nucleic acid strand to anneal or "attach" to each of the two template strands. To make sure this happens, the solution is held at an appropriate temperature, such as about 55° C. for about 15 seconds, in an "incubation" zone.

(4) The solution is then heated to and held at about 70° C., to cause an extension enzyme, preferably a thermostatable enzyme, to extend the primer strand bound to the template strand by using the nucleotides that are present.

(5) The completed new pair of strands is heated to 92°–95° C. again, for about 10–15 seconds, to cause this pair to separate.

(6) Steps (3)–(5) are then repeated, a number of times until the appropriate number of strands are obtained. The more repetitions, the greater the number of multiples of the nucleic acid (here, DNA) that is produced. Preferably the desired concentration of nucleic acid is reached in a minimum amount of time.

A cuvette is usually used to hold the solution while it passes through the aforementioned temperature stages. Depending upon the design given to the cuvette, it can proceed more or less rapidly through the various stages. A key aspect controlling this is the thermal transfer efficiency of the cuvette—that is, its ability to transfer heat more or less instantaneously to or from all of the liquid solution within the cuvette. The disposition and the thermal resistance of the liquid solution itself are usually the major aspects affecting the thermal transfer, since portions of the liquid solution that are relatively far removed from the heat source or sink, will take longer to reach the desired temperature.

The crudest and earliest type of cuvette used in the prior art is a test tube, which has poor thermal transfer efficiency since (a) the walls of the cuvette by being glass or plastic, do not transfer thermal energy well, and (b) a cylinder of liquid has relatively poor thermal transfer throughout the liquid. That is, not only does the liquid have low thermal conductivity, but also a cylinder of liquid has a low surface to volume ratio, that is, about 27 $in^{-1}$ for a fill of about 100 μl.

Still another problem in DNA amplification is the manner in which the cuvette alows for ready removal of the liquid after reaction is complete. A test tube configuration readily permits such removal. However, modification of the cuvette to provide better thermal transfer efficiency tends to reduce the liquid transferability. That is, a cuvette having capillary spacing only, permits rapid heating of the contents. However, the capillary spacing resists liquid removal.

RELATED APPLICATIONS

In commonly owned U.S. application Ser. No. 123,751 filed by Jeffrey L. Helfer et al, entitled "Cuvette", there is disclosed a cuvette that solves the aforementioned problems by providing for a thermal time constant for the cuvette and water contained therein, that is no greater than about 10 seconds. That invention, however, did not account for the fact that occasionally, the heating required for reactions in the cuvette generates pressures that cause the thermal conductive wall of the cuvette to flex, i.e., "dome" outward. Such flexing is unsatisfactory when it occurs, as it can interfere with proper contact with the heating element. Such interference, if it exists, reduces the rate at which thermal energy can be transferred to or from the cuvette and thereby adversely affects the thermal time constant of the fluid within the cuvette. Under the most severe conditions, the "doming" effect can also cause the thermally conductive wall to separate from the cuvette.

SUMMARY OF THE INVENTION

This invention provides a solution of the flexing problem noted above.

More specifically, this invention concerns a cuvette for controlled reaction of components of a liquid involving cycling through temperatures applied by a heater to the cuvette, the cuvette having a least one liquid-confining chamber defined by two spaced-apart opposing walls each providing a major surface of liquid contact; side walls connecting the two opposing walls; and means permitting the introduction of liquid into, and the removal of such liquid from, the chamber; one of the opposing walls comprising a thermally conductive material as the sole structural component, the thermal conductive material being exposed to the environment to permit contact with an external heater or cooler. The cuvette is improved in that the opposite one of the spaced-apart opposing walls has a flexural strength that is sufficiently less than that of the thermally conductive structural component, as to cause the opposite one of the walls to flex under internal pressure, in lieu of the thermal conductive structural component;

whereby the thermally conductive structural component substantially keeps its initial shape and contact with the heater or cooler, when the cuvette is applied to such heater/cooler.

Thus, it is an advantageous feature of the invention that a cuvette for rapid thermal cycling is provided, featuring a heat transfer wall sufficiently flexible as to flex under internal pressure, wherein means are provided to prevent such flexing.

It is a related advantageous feature of the invention that such a cuvette is provided wherein the wall opposite to the heat transfer wall is deliberately constructed to undergo deformation to relieve internal pressure, before the heat transfer wall becomes deformed.

Other advantageous features will become apparent upon reference to the following detailed description of the preferred embodiments, when read in light of the attached drawings.

DESCRIPTION OF THE PREFERRED EMBODIMENTS

The invention is described hereinafter for temperature cycling over a range of at least about 35° C., as is particularly useful in replicating DNA strands. In addition, it is also useful for any kind of reaction of liquid components and reagents that requires repetitive heating and cooling of the cuvette within which the reaction is conducted. It is further useful if the temperature range of cycling is more or less than 35° C.

Orientations such as "up", "down", "above" and "below" are used with respect to the cuvette as it is preferably used.

Figure 1:
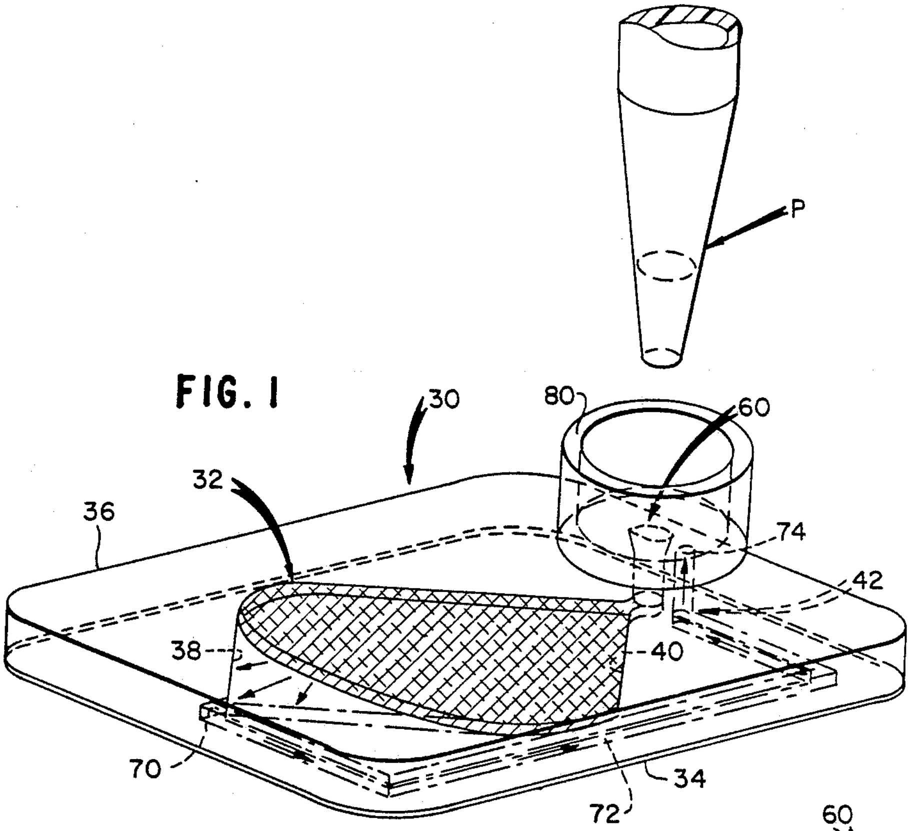
FIG. 1 is an isometric view of a cuvette with respect to which the present invention is an improvement.
Figure 2:
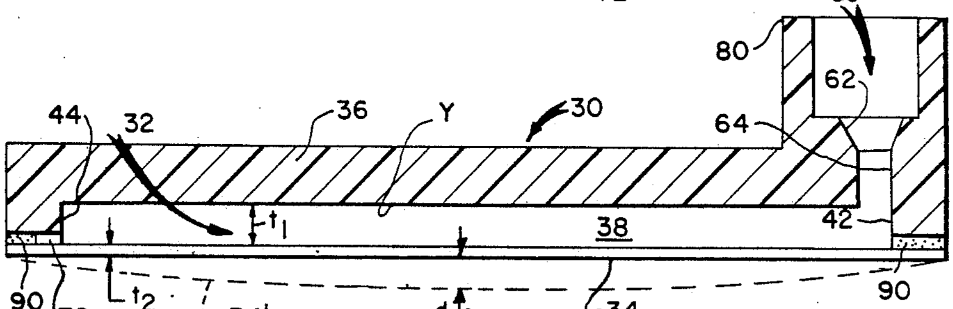
FIG. 2 Prior Art
FIG. 2 is a vertical section view taken generally along the mid-axis of the cuvette of FIG. 1.

Turning first to FIGS. 1–2, a cuvette 30 is shown constructed as described in the aforesaid commonly owned application. It comprises a liquid-confining chamber 32 defined by two opposing walls 34 and 36, FIG. 2, spaced apart a distance $t_1$. Such spacing is achieved by side walls 38 and 40, that join at opposite ends 42 and 44 of chamber 32. Most preferably, the shape of side walls 38 and 40 is one of a gradual concavity, so that they diverse at end 42, FIG. 1, at an angle of about 90° C., and at a point halfway between ends 42 and 44, start to reconverge again at an angle of about 90°. Distance $t_1$, FIG. 2, is selected such that such distance, when considered in light of the shape of sidewalls 38 and 40, minimizes the quantity of liquid that is retained in the cuvette upon removal of liquid. More specifically, that distance is selected, given the shape shown for walls 38 and 40, so that the capillary number ($N_{ca}$) and the goucher number ($N_{GO}$), both standard terms known in the fluid management art, are each less than 0.05. When so selected, momentum transfer particularly under a liquid-driven transfer system, results in a majority removal of liquid from chamber 32. Highly preferred values of $t_1$ are between about 0.5 mm and about 2.5 mm.

Walls 34 and 36 provide the major surfaces in contact with the liquid. As such, their surface area is selected such that, when considered in light of the thickness of spacing $t_1$, the surface-to-volume ratio for chamber 32 is optimized for a high rate of thermal energy transfer. A highly preferred example provides an exposed surface area of 2.4 $cm^2$ (0.37 $in^2$) for each of walls 34 and 36, with the surface from the side walls providing a contact area of about 0.36 $cm^2$. Most preferably, therefore, the surface-to-volume ratio is between about 65 $in^{-1}$ and about 130 $in^{-1}$ for a fill volume of between 200 and 100 μl, respectively.

Such a large fluid surface-to-volume ratio provides an advantage apart from a rapid thermal energy transfer. It means that, for a given volume, a much larger surface area is provided for coating reagents. This is particularly important for reagents that have to be coated in separate locations on the surface to prevent premature mixing, that is, mixing prior to injection of liquid within the chamber. Also, the large reagent/fluid interface area and short diffusion path provided by the large s/v ratio of the cuvette provides rapid reagent dissolution without requiring external excitation (such as shaking).

Therefore, one or more reagent layers (not shown) can be applied to the interior surface of wall 36, in a form that will allow it to enter into a reaction with liquid sample inserted into chamber 32. As used herein, "layer" includes reagents applied as discrete dots.

A liquid access aperture 60 is formed in wall 36 adjacent end 42, FIG. 2. The aperture has an upper portion 62 and a lower portion 64 that connects the upper portion with chamber 32. Preferably at least portion 62 is conical in shape, the slope of which allows a conical pipette P, FIG. 1, to mate therewith.

At opposite end 44, an air vent 70 is provided, in a manner similar to that described in U.S. Pat. No. 4,426,451. Most preferably, air vent 70 extends into a passageway 72, FIG. 1, that is routed back to a point adjacent end 42, where it terminates in opening 74 adjacent access aperture 60.

To allow a single closure device to seal both the access aperture 60 and opening 74 of the air vent, both of these are surrounded by a raised, cylindrical boss 80. Any conventional closure mechanism is useful with boss 80, for example, a stopper. Such stopper can have external threads for engaging mating internal threads, not shown, on the boss, or it can be constructed for a force fit within the boss 80.

The wall 34 opposite to wall 36 is the heat transfer wall, constructed with a predetermined thermal path length and thermal resistance that will provide a high rate of thermal energy transfer. Most preferably, such path length ($t_2$ in FIG. 2) is no greater than about 0.3 mm, and the thermal resistance is no greater than about 0.01° C./watt. These properties are readily achieved by constructing wall 34 out of a thermally conductive metal such as aluminum that is about 0.15 mm thick. Such aluminum has a thermal resistance R, calculated as thickness $\chi$.1/(conductivity K.surface area A), which is about 0.003° C./watt. (These values can be contrasted for ordinary glass of the same thickness, which has a thermal resistance of about 0.24° C./watt.)

Wall 34 can be secured to sidewalls 38 and 40 by any suitable means. One such means is a layer 90, FIG. 2, which comprises for example a conventional high temperature acrylic adhesive, and a conventional polyester adhesive. Most preferably, layer 90 does not extend over the surface area of wall 34, as such would greatly increase the thermal resistance of wall 34, and possibly interfere with reactions desired within chamber 32.

A cuvette constructed as described above for FIGS. 1–2, has been found to produce a thermal time constant tau ($\tau$) that is no greater than about 10 seconds. Most preferred are those in which $\tau$ is of the order of 3–8 seconds. When such a cuvette, filled with water, is heated along the exterior of wall 34, and its temperature is measured at point Y, FIG. 2, a thermal response curve is generated from 28° C. to a final temperature of 103.9° C. The time it takes for the liquid therein the reach a temperature of 76° C. (the initial temperature of 28° C. plus 63% of the difference (103.9−28)) is the value of tau ($\tau$). This derives (approximately) from the well-known thermal response equation:

$$\text{Temperature } T(t) = \text{Final Temperature (for time = infinity)} + (\text{Initial Temperature} - \text{Final Temperature}) \cdot e^{-t/\tau} \quad (1)$$

Thus, if the time interval t in question equals tau, then $e^{-t/\tau}=e^{-1}\neq 0.37$. In such a case, T (t) (at t=tau) is the temperature which is equal to the sum of the initial temperature plus 63% of (Final Temperature - Initial Temperature).

For the above-described cuvette, tau is about 3.5 seconds, for the liquid contained therein.

If the adhesive of layer 90 does extend over all the surface of wall 34, then tau can be increased to as much as 7 or 8 sec.

A problem occasionally occurs with cuvette 30, particularly at the high temperature end of the cycling. Pressure build-up occurs, due to thermal expansion of fluids and air within the cuvette as well as the release of gases dissolved in the liquid and the sealing of opening 60 as described above. In the cuvette of FIG. 2, this causes wall 34 to tend to deform outward, as indicated by the phantom line 34'. The outward deformation creates a dome of thickness which prevents cuvette 30 from properly resting on a flat heating element. That is, only a minor portion of surface 34' remains in contact with the heating element. Such dome formation thus reduces the rapid thermal transfer through wall 34 that is desired.

Figure 3:
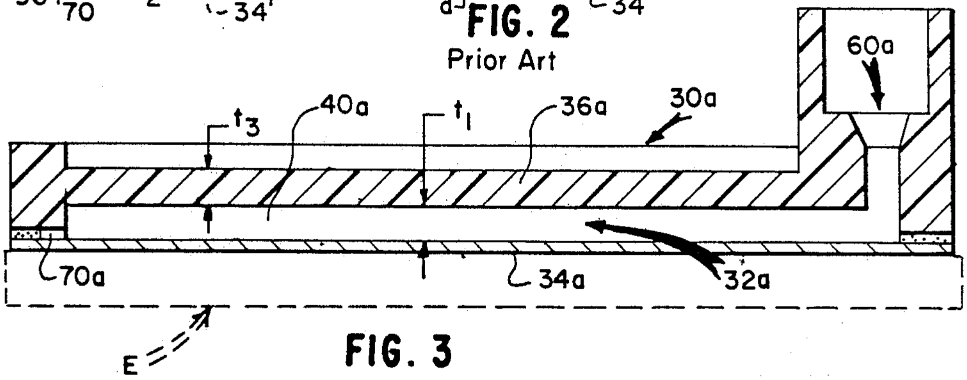
FIG. 3 is a section view similar to that of FIG. 2, but illustrating the invention.

In accord with the invention, FIG. 3, the aforementioned problems are solved by a cuvette in which a part thereof, other than the thermally conductive wall, becomes deformed to partially accommodate the pressure, in order to maintain intimate contact between reaction vessel wall 34 and the incubator. Parts similar to those previously described in FIGS. 1 and 2 bear the same reference numeral, to which the distinguishing suffix "a" is appended.

Thus, cuvette **30*a* comprises opposite major walls 34*a* and 36*a* defining, with side walls 40*a* (only one shown), a chamber 32*a* having a spacing $t_1$. These and the access aperture 60*a* and air vent 70*a* are generally constructed as described above. To insure that wall 34*a* does not deform under pressure, wall 36*a* is constructed to have a flexure strength that is less than that of wall 34*a*. Specifically, this is preferably done as follows: if wall 34*a*** comprises aluminum that is about 0.15 mm thick, then its flexure strength K at the center of flexure is determinable, based on the following:

Deflection X is determined by the well-known equation $$X=\alpha Pa^2/Et^3 \quad (2)$$

where P=total applied load, E=plate modulus of elasticity, t=plate thickness, and $\alpha$ is an empirical coefficient (usually equal to about 0.015). Rearranging, $$P/X=Et^3/\alpha a^2. \quad (3)$$

Because P/X is analogous to F/X which equals K (flexure strength), then $$K\neq Et^3/\alpha a^2. \quad (4)$$

This allows K to be calculated to be about $6.11\times10^6$ dynes/mm. For wall **36*a* to have a flexure strength less than that, for example a value no greater than about $1\times10^6$ dynes/mm, it need only comprise a layer of polyethylene or polypropylene that is about 0.3 mm thick (twice that of the aluminum wall 34*a*), to have a flexure strength of about $8.3\times10^5$ dynes/mm, calculated in the same manner. In such a construction, wall 36*a* will dome upwardly as pressure, such as 12 psi, is generated within chamber 32*a*, leaving wall 34*a*** lying planar against the heating element (shown in phantom as "E").

In use, the cuvette is filled to about point 44, FIG. 2, which provides a fill of about 90%, with a liquid containing the desired sample for reaction, for example, a solution of a DNA sequence that is to be amplified. The device is then inserted into an appropriate incubator and cycled through the necessary stages for the reaction.

Any suitable incubator is useful to cycle the cuvettes of this invention through the desired heating and cooling stages. Most preferably, the incubator provides stages that cycle through the temperatures described in the "Background" above. A convenient incubator for doing this is described in the aforesaid related application, the details of which are expressly incorporated herein by reference. Preferably it is one having the following stations: A preincubate station has heating means that delivers a temperature of 95° C. From there, the cuvette is pushed by conventional pusher means onto a ring of constant temperature stations, the first one of which is maintained at 55° C. From this station the cuvette is shuttled to the next adjacent, or second, station, which heats it to 70° C. This temperature is maintained for a period, and accordingly the third station is also at that temperature. Next, a short-time denaturing station (4th station) is encountered to denature the newly replicated DNA, which station is maintained at 95° C. Stations 5–12 simply repeat twice more the cycles already provided by stations 1 to 4. A moderate number of cycles through the incubator can take place before the cuvette is removed. The number of cycles depends on the concentration in the sample of the DNA sequence target desired to be amplified, and the desired final concentration. After station no. 12, a conventional transfer mechanism moves the cuvette off the ring for further processing. (Both the injection of liquid into the cuvette and the removal of liquid therefrom are done off-line, that is, outside of the incubator.)

The invention has been described in detail with particular reference to preferred embodiments thereof, but it will be understood that variations and modifications can be effected within the spirit and scope of the invention.

What is claimed is:

1. In a cuvette for controlled reaction of components of a liquid involving cycling through temperatures applied by a heater or cooler to the cuvette, the cuvette having at least one liquid-confining chamber defined by two spaced-apart opposing walls each providing a major surface of liquid contact; side walls connecting the two opposing walls; and means permitting the introduction of liquid into, and the removal of such liquid from, the chamber; one of the opposing walls comprising a thermally conductive material as the sole structural component, the thermally conductive material being exposed to the environment to permit contact with an external heater or cooler;

the improvement wherein the opposite one of said spaced-apart opposing walls has a flexural strength that is sufficiently less than that of said thermally conductive structural component, as to cause said opposite one of said walls to flex under internal pressure, in lieu of said thermally conductive structural component;

whereby said thermally conductive structural component substantially keeps its initial shape and contact with said heater, when the cuvette is applied to such heater or cooler.

2. A cuvette as defined in claim 1, wherein said thermally conductive structural component is aluminum; and said opposite wall has a flexural strength that is no greater than about $1 \times 10^6$ dynes/mm.

3. A cuvette as defined in claim 1, wherein the thermal time constant for a liquid within the cuvette is no greater than about 10 seconds.

* * * * *